(12) United States Patent
Gavish et al.

(10) Patent No.: US 8,485,982 B2
(45) Date of Patent: Jul. 16, 2013

(54) APPARATUS AND METHOD FOR BREATHING PATTERN DETERMINATION USING A NON-CONTACT MICROPHONE

(75) Inventors: Benjamin Gavish, Mevaseret Zion (IL); Yoram Doron, Gedera (IL)

(73) Assignee: Intercure Ltd. (IL)

( * ) Notice: Subject to any disclaimer, the term of this patent is extended or adjusted under 35 U.S.C. 154(b) by 1550 days.

(21) Appl. No.: 11/958,083

(22) Filed: Dec. 17, 2007

(65) Prior Publication Data

US 2009/0118631 A1 May 7, 2009

Related U.S. Application Data

(62) Division of application No. 11/572,483, filed as application No. PCT/IL2005/000778 on Jul. 21, 2005, now Pat. No. 7,850,619.

(60) Provisional application No. 60/590,508, filed on Jul. 23, 2004.

(51) Int. Cl.
*A61B 5/08* (2006.01)
*A61B 5/02* (2006.01)

(52) U.S. Cl.
USPC ............ 600/529; 600/484; 600/481; 600/500

(58) Field of Classification Search
USPC .................. 600/481, 483, 484, 529–543, 595
See application file for complete search history.

(56) References Cited

U.S. PATENT DOCUMENTS

| | | |
|---|---|---|
| 4,195,626 A | 4/1980 | Schweizer et al. |
| 4,312,358 A | 1/1982 | Barney |
| 4,450,843 A | 5/1984 | Barney et al. |
| 4,571,680 A | 2/1986 | Wu |
| 4,711,585 A | 12/1987 | Fresquez et al. |
| 4,776,323 A | 10/1988 | Spector |
| 4,798,538 A | 1/1989 | Yagi et al. |
| 4,883,067 A | 11/1989 | Knispel et al. |
| 5,027,686 A | 7/1991 | Ishikawa et al. |
| 5,076,281 A | 12/1991 | Gavish et al. |
| 5,137,501 A | 8/1992 | Mertesdorf |
| 5,143,078 A | 9/1992 | Mather et al. |

(Continued)

FOREIGN PATENT DOCUMENTS

| | | |
|---|---|---|
| CN | 1320054 | 10/2001 |
| EP | 856334 A2 | 8/1998 |

(Continued)

OTHER PUBLICATIONS

An Office Action dated Jun. 24, 2011, which issued during the prosecution of U.S. Appl. No. 12/427,183.

(Continued)

*Primary Examiner* — Navin Natnithithadha
(74) *Attorney, Agent, or Firm* — St. Onge Steward Johnston & Reens LLC

(57) ABSTRACT

A method is provided for analyzing respiration of a subject (20). Using a non-contact microphone (22), a raw signal indicative of airflow sounds of the respiration is generated. The raw signal is analyzed to determine a first set of one or more parameters of the respiration. An algorithm is applied to the first set of parameters to derive a second set of one or more estimated parameters of the respiration that are not generally directly measurable in the raw signal. Other embodiments are also described.

18 Claims, 6 Drawing Sheets

U.S. PATENT DOCUMENTS

| | | | |
|---|---|---|---|
| 5,195,528 A | 3/1993 | Hok et al. | |
| 5,267,942 A | 12/1993 | Saperston | |
| 5,423,328 A | 6/1995 | Gavish et al. | |
| 5,434,871 A | 7/1995 | Purdham et al. | |
| 5,465,729 A | 11/1995 | Bittman et al. | |
| 5,509,414 A | 4/1996 | Hok et al. | |
| 5,533,947 A | 7/1996 | Tomlinson et al. | |
| 5,592,143 A | 1/1997 | Romney et al. | |
| 5,596,994 A | 1/1997 | Bro | |
| 5,662,117 A | 9/1997 | Bittman | |
| 5,671,733 A | 9/1997 | Raviv et al. | |
| 5,678,571 A | 10/1997 | Brown | |
| 5,687,291 A * | 11/1997 | Smyth | 706/10 |
| 5,734,090 A | 3/1998 | Koppel et al. | |
| 5,797,852 A | 8/1998 | Karakasoglu et al. | |
| 5,800,337 A | 9/1998 | Gavish et al. | |
| 5,827,179 A | 10/1998 | Lichter et al. | |
| 5,830,107 A | 11/1998 | Brigliadoro | |
| 5,921,890 A | 7/1999 | Miley et al. | |
| 6,001,048 A | 12/1999 | Taylor | |
| 6,001,065 A | 12/1999 | DeVito | |
| 6,013,007 A | 1/2000 | Root et al. | |
| 6,090,037 A | 7/2000 | Gavish et al. | |
| 6,092,058 A * | 7/2000 | Smyth | 706/10 |
| 6,150,941 A | 11/2000 | Geiger et al. | |
| 6,212,135 B1 | 4/2001 | Schreiber | |
| 6,230,047 B1 | 5/2001 | McHugh | |
| 6,241,683 B1 | 6/2001 | Macklem et al. | |
| 6,251,048 B1 | 6/2001 | Kaufman | |
| 6,261,238 B1 | 7/2001 | Gavriely et al. | |
| 6,478,736 B1 | 11/2002 | Mault | |
| 6,519,567 B1 | 2/2003 | Fujii | |
| 6,582,342 B2 | 6/2003 | Kaufman | |
| 6,662,032 B1 | 12/2003 | Gavish et al. | |
| 6,672,991 B2 | 1/2004 | O'Malley | |
| 6,726,636 B2 | 4/2004 | Der Ghazarian et al. | |
| 6,746,247 B2 | 6/2004 | Barton | |
| 6,808,473 B2 | 10/2004 | Hisano et al. | |
| 6,902,513 B1 | 6/2005 | McClure | |
| 7,455,622 B2 | 11/2008 | Watterson et al. | |
| 7,521,623 B2 | 4/2009 | Bowen | |
| 7,544,880 B2 | 6/2009 | Takai et al. | |
| 7,616,097 B1 | 11/2009 | Whang | |
| 7,683,252 B2 | 3/2010 | Oliver et al. | |
| 7,705,230 B2 | 4/2010 | Bowen | |
| 7,728,215 B2 | 6/2010 | Miyajima et al. | |
| 7,737,353 B2 | 6/2010 | Sasaki et al. | |
| 7,738,935 B1 * | 6/2010 | Turcott | 600/336 |
| 7,745,716 B1 | 6/2010 | Murphy | |
| 7,766,794 B2 | 8/2010 | Oliver et al. | |
| 7,771,320 B2 | 8/2010 | Riley et al. | |
| 7,789,800 B1 | 9/2010 | Watterson et al. | |
| 7,805,150 B2 | 9/2010 | Graham et al. | |
| 7,841,967 B1 | 11/2010 | Kahn et al. | |
| 7,867,142 B2 | 1/2011 | Kim et al. | |
| 7,872,188 B2 | 1/2011 | Willis | |
| 7,927,253 B2 | 4/2011 | Vincent et al. | |
| 7,942,824 B1 * | 5/2011 | Kayyali et al. | 600/538 |
| 7,973,231 B2 | 7/2011 | Bowen | |
| 7,985,164 B2 | 7/2011 | Ashby | |
| 8,017,853 B1 | 9/2011 | Rice | |
| 8,029,415 B2 | 10/2011 | Ashby et al. | |
| 8,033,959 B2 | 10/2011 | Oleson et al. | |
| 8,038,576 B2 | 10/2011 | Farinelli et al. | |
| 8,082,920 B2 | 12/2011 | Hughes | |
| 8,101,843 B2 | 1/2012 | Turner | |
| 8,105,208 B2 | 1/2012 | Oleson et al. | |
| 8,162,804 B2 | 4/2012 | Tagliabue | |
| 8,183,453 B2 | 5/2012 | Wagner | |
| 8,200,323 B2 | 6/2012 | DiBenedetto et al. | |
| 8,221,290 B2 | 7/2012 | Vincent et al. | |
| 8,241,184 B2 | 8/2012 | DiBenedetto et al. | |
| 8,251,874 B2 | 8/2012 | Ashby et al. | |
| 8,298,123 B2 | 10/2012 | Hickman | |
| 8,311,654 B2 | 11/2012 | Sako et al. | |
| 2001/0054270 A1 | 12/2001 | Rice | |
| 2002/0040601 A1 | 4/2002 | Fyfe et al. | |
| 2002/0042328 A1 | 4/2002 | Yoo | |
| 2003/0059750 A1 | 3/2003 | Bindler et al. | |
| 2003/0171189 A1 | 9/2003 | Kaufman | |
| 2004/0077934 A1 | 4/2004 | Massad | |
| 2004/0116784 A1 | 6/2004 | Gavish | |
| 2004/0127335 A1 | 7/2004 | Watterson et al. | |
| 2005/0113703 A1 | 5/2005 | Farringdon et al. | |
| 2005/0126370 A1 | 6/2005 | Takai et al. | |
| 2005/0215397 A1 | 9/2005 | Watterson et al. | |
| 2006/0084551 A1 | 4/2006 | Volpe | |
| 2006/0102171 A1 | 5/2006 | Gavish | |
| 2006/0107822 A1 | 5/2006 | Bowen | |
| 2006/0111621 A1 | 5/2006 | Coppi et al. | |
| 2006/0169125 A1 | 8/2006 | Ashkenazi et al. | |
| 2006/0243120 A1 | 11/2006 | Takai et al. | |
| 2006/0277474 A1 | 12/2006 | Robarts et al. | |
| 2007/0029059 A1 | 2/2007 | Elgarhy et al. | |
| 2007/0033295 A1 | 2/2007 | Marriott | |
| 2007/0044641 A1 | 3/2007 | McKinney et al. | |
| 2007/0060446 A1 | 3/2007 | Asukai et al. | |
| 2007/0074618 A1 | 4/2007 | Vergo | |
| 2007/0113725 A1 | 5/2007 | Oliver et al. | |
| 2007/0113726 A1 | 5/2007 | Oliver et al. | |
| 2007/0118043 A1 | 5/2007 | Oliver et al. | |
| 2007/0135264 A1 | 6/2007 | Rosenberg | |
| 2007/0169614 A1 | 7/2007 | Sasaki et al. | |
| 2007/0203665 A1 | 8/2007 | Darley et al. | |
| 2007/0208531 A1 | 9/2007 | Darley et al. | |
| 2007/0270667 A1 | 11/2007 | Coppi et al. | |
| 2008/0076637 A1 | 3/2008 | Gilley et al. | |
| 2008/0077619 A1 | 3/2008 | Gilley et al. | |
| 2008/0077620 A1 | 3/2008 | Gilley et al. | |
| 2008/0090703 A1 | 4/2008 | Rosenberg | |
| 2008/0096726 A1 | 4/2008 | Riley et al. | |
| 2008/0171943 A1 | 7/2008 | Farringdon et al. | |
| 2008/0183090 A1 | 7/2008 | Farringdon et al. | |
| 2008/0188354 A1 | 8/2008 | Pauws et al. | |
| 2008/0214358 A1 | 9/2008 | Ogg et al. | |
| 2008/0254946 A1 | 10/2008 | Pauws et al. | |
| 2008/0300109 A1 | 12/2008 | Karkanias et al. | |
| 2008/0306619 A1 | 12/2008 | Cerra et al. | |
| 2009/0024233 A1 | 1/2009 | Shirai et al. | |
| 2009/0054741 A1 | 2/2009 | McAleer | |
| 2009/0088876 A1 | 4/2009 | Conley et al. | |
| 2009/0139389 A1 | 6/2009 | Bowen | |
| 2009/0260506 A1 | 10/2009 | Saperston | |
| 2009/0270744 A1 | 10/2009 | Prstojevich et al. | |
| 2010/0037753 A1 | 2/2010 | Wagner | |
| 2010/0186578 A1 | 7/2010 | Bowen | |
| 2010/0217099 A1 | 8/2010 | LeBoeuf et al. | |
| 2010/0279825 A1 | 11/2010 | Riley et al. | |
| 2010/0286532 A1 | 11/2010 | Farringdon et al. | |
| 2011/0003665 A1 | 1/2011 | Burton et al. | |
| 2011/0016120 A1 | 1/2011 | Haughay et al. | |
| 2011/0054290 A1 | 3/2011 | Derchak | |
| 2012/0094806 A1 | 4/2012 | Danford | |
| 2012/0225412 A1 | 9/2012 | Wagner | |

FOREIGN PATENT DOCUMENTS

| | | |
|---|---|---|
| WO | WO9814116 A3 | 8/1998 |
| WO | WO0059580 A1 | 10/2000 |
| WO | WO0102049 A2 | 1/2001 |
| WO | WO-0119243 | 3/2001 |
| WO | WO-0213697 | 2/2002 |
| WO | 2004/014226 | 2/2004 |

OTHER PUBLICATIONS

U.S. Appl. No. 60/590,508.

W. H. Cooke, et al., "Controlled Breathing Protocols Probe Human Autonomic Cardiovascular Rhythms", American Journal of Physiology, 1998, 274:H709-H718.

A Supplementary European Search Report dated Nov. 2, 2010, which issued during the prosecution of Applicant's European Patent Application No. EP03784453.

A Translation of an Office Action dated Jan. 26, 2011, which issued during the prosecution of Applicant's Japanese Patent Application No. JP 2007-522123.

An Examination Report dated Nov. 2, 2010, which issued during the prosecution of Applicant's European Patent Application No. EP 05762105.4.

An Office Action dated Dec. 12, 2008, which issued during prosecution of Applicant's Chinese Patent Application No. 200580032171.1.

Nishida Y et al., "A non-invasive and unrestrained monitoring of human respiratory system by sensorized environment", Proc. of the IEEE Sensors 2002, Orlando, FL, Jun. 12-14, 2002.

A Supplementary European Search Report dated Dec. 10, 2008, which issued during the prosecution of Applicant's European Patent Application No. Ep 05 76 2105.

An Office Action dated Dec. 28, 2012, which issued during the prosecution of U.S. Appl. No. 13/471,582.

* cited by examiner

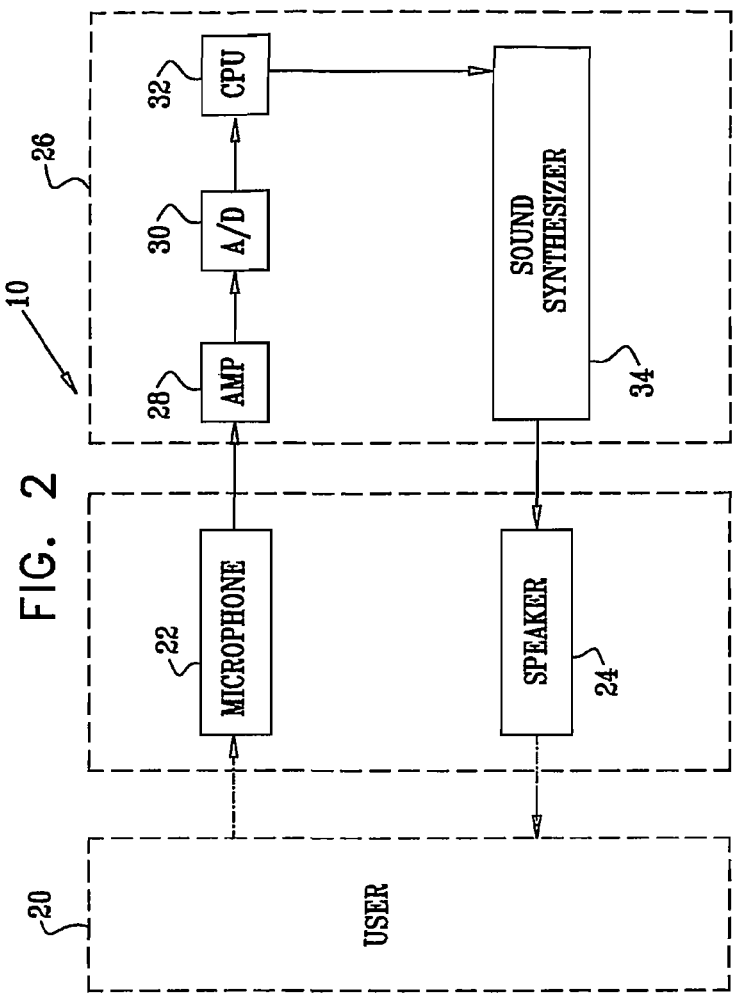
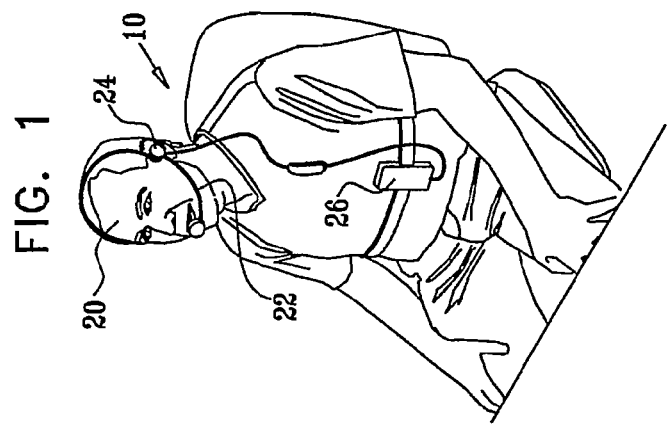

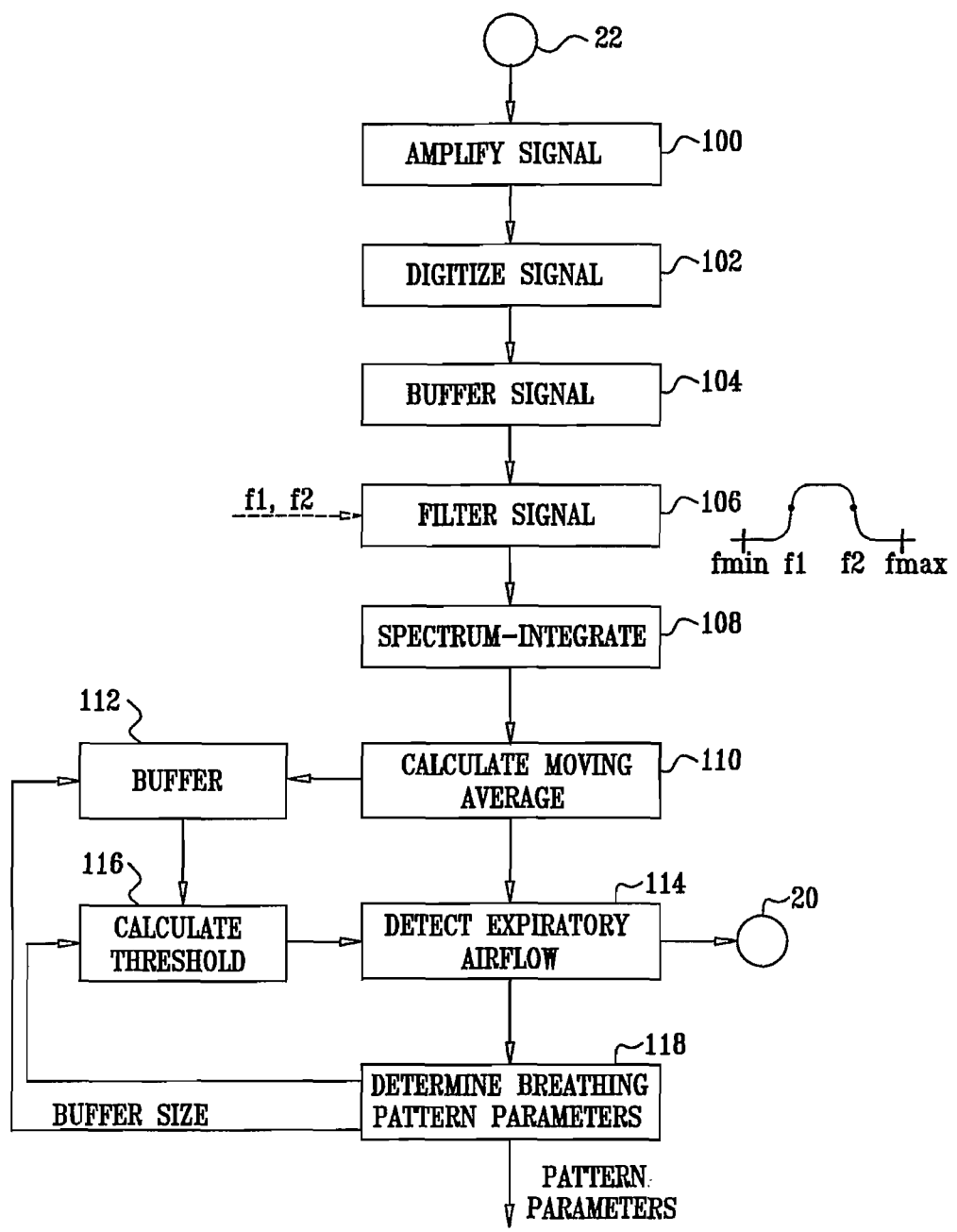

APPARATUS AND METHOD FOR BREATHING PATTERN DETERMINATION USING A NON-CONTACT MICROPHONE

CROSS-REFERENCE TO PRIOR APPLICATIONS

This application is a divisional of U.S. patent application Ser. No. 11/572,483, filed May 31 2007, which is the U.S. National Phase of PCT/IL2005/000778 filed Jul. 21, 2005, which claims the benefit of U.S. Provisional Patent Application Ser. No. 60/590,508, filed Jul. 23, 2004, which is assigned to the assignee of the present application and is incorporated herein by reference. The International Application was published on Jan. 26, 2006 as WO 2006/008745 A2 under PCT Article 21(2).

FIELD OF THE INVENTION

The present invention relates generally to medical devices, and specifically to devices that monitor and/or modify biorhythmic activity of a user.

BACKGROUND OF THE INVENTION

Physical exercise often involves modifying a multi-phase biorhythmic activity, such as breathing. Breathing patterns display irregularities in a number of cardiovascular diseases, including congestive heart failure (CHF), and pulmonary diseases, including chronic obstructive pulmonary disease (COPD). These irregularities are known markers for disease-related mortality and morbidity. Typical irregularities include Cheyne-Stokes breathing (recurrent episodes of central apnea alternating with hyperpnea), amplitude-modulated breathing (periodic breathing) at a rate of about one modulation per minute, repeated sighs, and breathing at random amplitudes and periods. A reduction in breathing pattern irregularity indicates an improvement in health. The impairment of cardiovascular reflexes, which control blood pressure and volume in an attempt to minimize fluctuations in blood supply to organs, is also clinically significant in cardiovascular and psychosomatic diseases.

U.S. Pat. Nos. 5,076,281, 5,800,337, and 6,090,037 to Gavish, which are incorporated herein by reference, describe methods and devices for modifying biorhythmic activity by measuring one or more variables of a user. The patents describe the generation of a stimulus, which is provided to the user, so as to change the biorhythmic activity of a user in a way that relates in a predetermined way to the monitored biorhythmic activity. The '037 additionally describes a respiration sensor.

U.S. Pat. No. 5,423,328 to Gavish, which is incorporated herein by reference, describes a stress-detecting device for monitoring respiration, and, in particular, a method for detecting and monitoring circumferential changes in the chest or abdomen of a user resulting from breathing.

U.S. Pat. No. 6,662,032 to Gavish et al., which is incorporated herein by reference, describes techniques for facilitating improving health of a user, including a first sensor, adapted to measure a first physiological variable, which is indicative of a voluntary action of the user; a second sensor, adapted to measure a second physiological variable, which is not entirely under the direct voluntary control of the user; and circuitry, adapted to receive respective first and second sensor signals from the first and second sensors, and responsive thereto, to generate an output signal which directs the user to modify a parameter of the voluntary action.

U.S. Patent Application Publication 2004/0116784 to Gavish, which is incorporated herein by reference, describes apparatus including a sensor, adapted to generate a sensor signal indicative of biorhythmic activity of a user of the apparatus, the sensor signal having a first characteristic, indicative of a voluntary action of the user, and a second characteristic, indicative of a benefit-related variable of the user.

PCT Publication WO 04/014226 to Gavish, which is incorporated herein by reference, describes apparatus including a memory for storing a set of computer instructions, the memory adapted to have stored therein an initial form of a multi-phase biorhythmic activity pattern and an indication of a desired form of the multi-phase biorhythmic activity pattern, wherein a ratio of durations of two phases in the desired form is different from a ratio of durations of the respective phases in the initial form, and wherein at least one phase of the multi-phase biorhythmic activity pattern corresponds to a respective phase of a multi-phase biorhythmic activity of the subject.

Intercure, Inc. (Fort Lee, N.J., USA and Lod, Israel) markets RESPeRATE™, a device that utilizes some of the techniques described in the above-referenced patents and patent application publications. This device for modifying biorhythmic activity includes an input for the respiration signal, a central processing unit, memory, a sound synthesizing chip, and output to earphones.

U.S. Pat. No. 5,734,090 to Koppel et. al., which is incorporated herein by reference, describes a method and apparatus for verifying an expiratory breath flow (e.g., for determining a degree of alcohol in the breath), utilizing the sonic characteristics of a standardized breath as a reference.

U.S. Pat. No. 6,726,636 to Der Ghazarian et al., which is incorporated herein by reference, describes a voice recognition breathalyzer comprising a microphone for transducing spoken expression into electronic signals and a breathalyzer sensor for transducing a given breath content into electronic signals.

U.S. Pat. No. 5,509,414 to Hok, which is incorporated herein by reference, describes techniques for detecting air flow at the mouth and nose of a subject, including a transducer for converting electrical signals into ultrasound waves and vice versa, means for directing the ultrasound waves toward the mouth and nose of the subject and receiving return waves, and a detector to analyze electrical signals converted by the transducer from the return ultrasound waves.

U.S. Pat. No. 5,195,528 to Hok, which is incorporated herein by reference, describes an acoustic respiration detector including at least two tubular air transmission lines having ends which are connected to microphone elements. Close to the other ends of the lines are openings at which turbulence, and hence acoustic signals, are created by the incidence of airflow caused by respiration. A holding element secures the openings relative to the mouth or nose of a patient whose respiratory function is to be monitored, and a flow-directing element, for example formed like a face mask, directs the airflow to the openings. The microphone elements are connected in a bridge circuit with two voltage supplying leads and at least one signal lead. This arrangement is described as suppressing sensitivity to mechanical and acoustic disturbances.

U.S. Pat. No. 5,797,852 to Karakasoglu et al., which is incorporated herein by reference, describes sleep apnea screening and/or detection apparatus for use by a patient breathing through the nose and/or mouth and producing an air flow into and out of the lungs of the patient and creating audible sounds.

U.S. Pat. No. 6,150,941 to Geiger et al., which is incorporated herein by reference, describes a stand-off, non-invasive acoustic detector for monitoring physical activity and/or breathing activity of children and infants.

U.S. Pat. No. 6,261,238 to Gavriely, which is incorporated herein by reference, describes a method for analyzing breath sounds produced by a respiratory system, the method comprising: measuring breath sounds produced by the respiratory system; tentatively identifying a signal as being caused by a breath sound of a given type if it meets a first criteria characteristic of the breath sound of the given type; and confirming said identification if a tentatively identified signal meets a second criteria characteristic of the breath sound of the given type.

The following patents, all of which are incorporated herein by reference, may be of interest:

U.S. Pat. No. 4,195,626 to Schweizer
U.S. Pat. No. 5,678,571 to Brown
U.S. Pat. No. 5,596,994 to Bro
U.S. Pat. No. 4,883,067 to Knispel et al.
U.S. Pat. No. 4,798,538 to Yagi
U.S. Pat. No. 5,827,179 to Lichter et al.
U.S. Pat. No. 6,001,065 to DeVito
U.S. Pat. No. 5,921,890 to Miley
U.S. Pat. No. 5,027,686 to Ishikawa
U.S. Pat. No. 6,212,135 to Schreiber
U.S. Pat. No. 4,711,585 to Fresquez et al.

The following articles, all of which are incorporated herein by reference, may be of interest:

Cooke et al., "Controlled breathing protocols probe human autonomic cardiovascular rhythms," American Journal of Physiology 274:H709-H718 (1998)

Pitzalis et al., "Effect of respiratory rate on the relationship between RR interval and systolic blood pressure fluctuations: a frequency-dependent phenomenon," Cardiovascular Research 38:332-339 (1998)

Bernardi et al., "Effect of breathing rate on oxygen saturation and exercise performance in chronic heart failure," The Lancet 351:1308-1311 (1998)

Mortara et al., "Abnormal awake respiratory patterns are common in chronic heart failure and may prevent evaluation of autonomic tone by measures of heart rate variability," Circulation 96:246-252 (1997)

La Rovere et al., "Baroreflex sensitivity and heart-rate variability in prediction of total cardiac mortality after myocardial infarction," The Lancet 351:478-484 (1998)

SUMMARY OF THE INVENTION

In some embodiments of the present invention, a method is provided for determining a set of parameters of a breathing pattern of a user using a standard non-contact microphone. The method comprises using the microphone to measure a first subset of one or more parameters of respiration by the user, and applying an algorithm to the first subset of parameters in order to derive a second subset of one or more estimated parameters of the respiration that are not generally directly measurable using the microphone. The second subset of parameters is typically not directly measurable using the microphone because sounds associated with the second subset, if any, cannot be detected by the microphone and/or distinguished from background noise. For some applications, the algorithm is applied by setting the second subset of estimated parameters equal to a phenomenological function of the first set of parameters.

Typically, the first subset of parameters includes active expiration time (i.e., duration of active expiration) and breathing period (i.e., time between successive breaths), and the second subset of parameters includes inspiration time. Active expiration time is typically measured by detecting low-frequency sounds generated by expiratory airflow. The method enables the determination of inspiration time, which generally cannot be directly measured using a standard non-contact microphone, at least in part because inspiratory airflow is too quiet to be detected under normal background noise conditions.

In some embodiments of the present invention, a method is provided for improving biorhythmic signal detection in the presence of potentially variable background signal noise. The method comprises calibrating one or more signal detection parameters by guiding a user through a plurality of biorhythmic activity phases, and measuring the biorhythmic signal during the plurality of phases. The signal detection parameters typically include a signal-to-noise ratio and/or filtering characteristics. The signal detection parameters are used for filtering background noise from detected biorhythmic signals.

In some embodiments, the biorhythmic activity includes respiration, which is detected using a standard non-contact microphone. The user is guided to inhale for a certain period of time, exhale for a certain period of time, and, optionally, to hold his breath for a certain period of time. The signal detection parameters are typically calibrated by (a) determining signal characteristics of the background noise plus the sounds of inhalation, and the background noise plus the sounds of exhalation, and (b) using these signal characteristics to determine net background noise, and/or signal characteristics of the sounds of exhalation. Such signal characteristics of the sounds of exhalation are typically used to determine one or more of the signal detection parameters. For some applications, this method is used in conjunction with techniques for breathing pattern modification, such as those described in the above-mentioned patents and patent application publications to Gavish and Gavish et al.

These techniques for improving respiration signal detection enable the determination of specific signal detection parameters for each user under specific conditions of use. Such parameters typically vary from user to user based on the user's individual breathing habits (such as whether the user inspires and expires from the nose or from the mouth, and whether the user closes his lips during inspiration and expiration). These techniques enable dynamic determination of signal detection parameters during daily life in noisy environments.

For some applications, an algorithm is implemented for evaluating one or more parameters of a non-expiratory portion of the signal substantially continuously. For example, such parameters may include a duration or an amplitude of the non-expiratory portion. In an embodiment, these parameters are determined responsively to a physiological constraint to which most people typically adhere. One such constraint reflects the body's natural tendency to keep ventilation generally constant while minimizing energy expended. A practical example of this constraint is that following a relatively deep breath (which transiently increases ventilation), a subsequent breath is typically delayed.

In some embodiments of the present invention, the techniques described herein are implemented using the standard non-contact microphone of a conventional consumer electronics device, such as a telephone, cellular telephone, personal digital assistant (PDA), or portable digital audio player, which a user may have already purchased for other purposes. For a cellular telephone, for example, the user may speak directly into the microphone incorporated into the body of the phone, or, alternatively, the user may speak into an external microphone which plugs into the body of the phone. In general, a microphone may be used which is incorporated into the body of the consumer electronics device, or which is attached to the body of the consumer electronics device (e.g., by wire or wirelessly). Typically, the techniques described herein are implemented in software that is installed in such a device, and/or in a central location that is accessed by the device over a conventional wireless or wired network.

In some embodiments of the present invention, the techniques described herein are implemented using a non-contact microphone that is integrated into a medical device in fluid communication (e.g., via air or another gas) with respiration-related airflow of the subject. For example, the medical device may comprise a breathing mask or a tube, such as a tracheotomy tube.

For some applications, the breathing mask or tube are components of a ventilator that applies positive pressure to the lungs of the subject. The techniques described herein are used to detect proper performance of the ventilator, typically by detecting active expiration by the subject. Active expiration is typically measured by detecting low-frequency sounds indicative of expiratory airflow, rather than by detecting sounds of breathing. (In such subject, sounds of breathing often do not correlate with expiration, because the sounds of breathing are often affected by various constrictions in the subject's airways. However, low-frequency sounds indicative of expiratory airflow are not generally affected by such constrictions.) For some applications, the techniques described herein are used for non-contact monitoring of breathing during weaning from ventilation.

In an embodiment of the present invention, the techniques described herein are used for non-contact monitoring of breathing during use of a drug inhaler by the subject. For some applications, such non-contact monitoring of breathing is combined with techniques for modifying breathing activity of the subject, such as those described in the above-mentioned patent and patent application publications to Gavish and Gavish et al.

In an embodiment of the present invention, the techniques described herein and/or in the above-mentioned patent and patent application publications to Gavish and Gavish et al. are used to treat a subject suffering from insomnia. Insomnia is sometimes caused by disordered breathing, such as fast and shallow breathing. For some applications, insomnia is treated using techniques described herein for detecting and monitoring breathing, in combination with techniques for modifying respiration-related biorhythmic activity of the subject described in the above-mentioned patent and patent application publications to Gavish and Gavish et al.

In an embodiment of the present invention, the breathing monitoring techniques described herein are used for detecting sleep-disordered breathing, such as sleep-disordered breathing associated with sleep apnea or sudden infant death syndrome (SIDS). Typically, breath-by-breath airflow during exhalation is monitored. For some applications, such non-contact monitoring of breathing is combined with techniques for modifying breathing activity of the subject, such as those described in the above-mentioned patent and patent application publications to Gavish and Gavish et al.

There is therefore provided, in accordance with an embodiment of the present invention, a method for analyzing respiration of a subject, the method including:

using a non-contact microphone, detecting airflow sounds of the respiration, and converting the sounds into a signal;

analyzing the signal to determine a first set of one or more parameters of the respiration; and applying an algorithm to the first set of parameters to derive a second set of one or more estimated parameters of the respiration that are not generally directly measurable in the signal.

In an embodiment:

the first set of parameters includes an active expiration time and a breathing period of the respiration, the second set of parameters includes an inspiration time of the respiration, analyzing the signal includes analyzing the signal to determine the active expiration time and the breathing period, and applying the algorithm includes applying the algorithm to derive the inspiration time.

There is further provided, in accordance with an embodiment of the present invention, a method for analyzing respiration of a subject, the method including:

detecting airflow sounds of the respiration, and converting the sounds into a signal;

guiding the user through a plurality of respiration phases;

analyzing the signal during the guided respiration phases, and defining one or more parameters of a filter responsively to the analysis; and filtering background noise from the signal using the filter having the defined parameters.

In an embodiment, guiding the user includes guiding the user through inspiratory and expiratory respiration phases.

There is also provided, in accordance with an embodiment of the present invention, a method for modifying naturally-occurring multi-phase biorhythmic activity of a subject, the method including:

detecting a signal indicative of the multi-phase biorhythmic activity;

analyzing the signal to determine one or more parameters of a filter;

filtering background noise from the signal using the filter having the parameters;

at least in part responsively to the filtered signal, determining a stimulus input which is operative to change at least one aspect of the biorhythmic activity of the subject; and providing the stimulus input to the subject.

For some applications, filtering the background noise includes frequency filtering the signal. Alternatively or additionally, filtering the background noise includes performing non-frequency spectral analysis on the signal in order to classify the signal according to one or more variables.

In an embodiment, the background noise is indicative of secondary biorhythmic activity different from the multi-phase biorhythmic activity, and filtering the background noise from the signal includes filtering the secondary biorhythmic activity-related background noise from the signal.

In an embodiment, the multi-phase biorhythmic activity includes respiration of the subject, and detecting the signal includes detecting the signal indicative of the respiration. For some applications, the background noise includes a heartbeat-related component of the signal, and filtering the background noise from the signal includes filtering the heartbeat-related component from the signal.

In an embodiment, filtering the background noise includes performing spectral analysis on the signal to produce a frequency spectrum. For some applications, performing the spectral analysis includes frequency filtering the frequency spectrum.

For some applications, filtering the background noise includes removing non-frequency-related noise from the signal. For some applications, the non-frequency-related noise includes a heartbeat-related component of the signal, and removing the non-frequency-related noise includes removing the heartbeat-related component of the signal from the signal.

There is further provided, in accordance with an embodiment of the present invention, a method for analyzing respiration of a subject, the method including:

using a non-contact microphone, generating a raw signal indicative of airflow sounds of the respiration;

analyzing the raw signal to determine a first set of one or more parameters of the respiration; and applying an algorithm to the first set of parameters to derive a second set of one or more estimated parameters of the respiration that are not generally directly measurable in the raw signal.

In an embodiment, applying the algorithm includes setting the second set of one or more estimated parameters equal to a phenomenological function of the first set of one or more parameters.

In an embodiment, the first set of parameters includes a measure of breathing amplitude of the respiration, and analyzing the raw signal includes integrating the airflow sounds for a breath of the respiration to determine the measure of breathing amplitude. For some applications, the first set of parameters includes a measure of breathing amplitude of the respiration, the second set of parameters is selected from the list consisting of: a measure of ventilation of the subject, and a measure of breathing irregularity of the subject, and applying the algorithm includes applying the algorithm to the measure of breathing amplitude to derive the selected second set of parameters.

For some applications, the method includes analyzing at least one of the first and second sets of parameters to derive at least one additional breathing-related parameter of the subject selected from the list consisting of: breathing amplitude, a geometrical property of airflow of the subject, a characteristic of the airflow indicative of pursed lips breathing, a characteristic of the breathing indicative of relaxed breathing, a characteristic of the breathing indicative of passive elastic recoil of lungs of the subject, a characteristic of breathing with effort, and a characteristic of breathing during which the lungs of the subject undergo a functional change.

In an embodiment, the method includes guiding the subject to perform breathing in a plurality of respiration phases determined at least in part responsively to the second set of parameters. For some applications, guiding the subject to perform the breathing includes treating insomnia of the subject by guiding the subject to perform the breathing in the plurality of respiration phases.

In an embodiment, the non-contact microphone includes a non-contact microphone of a consumer electronics device capable of performing at least one function that does not facilitate analyzing respiration of the subject, and generating the raw signal includes using the non-contact microphone. In an alternative embodiment, the non-contact microphone is integrated into a medical device in fluid communication with respiration-related airflow of the subject, and generating the raw signal includes using the integrated non-contact microphone. For example, the medical device may include a drug inhaler, and generating the raw signal includes using the non-contact microphone integrated into the drug inhaler.

In an embodiment, analyzing the raw signal includes deriving an expiratory airflow sound signal from the raw signal, and analyzing the expiratory airflow sound signal to determine the first set of parameters. For some applications, the method includes generating a real-time indication for the subject that indicates whether expiration has been detected.

In an embodiment, the first set of parameters includes an active expiration time and a breathing period of the subject, and analyzing the expiratory airflow sound signal includes analyzing the expiratory airflow sound signal to determine the active expiration time and the breathing period. For some applications, the second set of parameters includes an amplitude of a non-expiratory portion of the respiration, and applying the algorithm includes applying the algorithm to derive the amplitude of the non-expiratory portion of the respiration.

In an embodiment, the second set of parameters includes an inspiration time of the subject, and applying the algorithm includes applying the algorithm to derive the inspiration time.

In an embodiment, applying the algorithm to derive the inspiration time includes determining whether a difference between the breathing period and the active expiration time is greater than or equal to a first function of the active expiration time, responsively to a positive determination, setting the inspiration time equal to a second function of the difference, and responsively to a negative determination, setting the inspiration time equal to a third function of the active expiration time.

For some applications, determining includes determining whether the difference between the breathing period and the active expiration time is greater than or equal to the active expiration time.

For some applications, setting responsively to the positive determination includes setting the inspiration time equal to a value within plus or minus 20% of the difference, such as within plus or minus 10% of the difference. For some applications, the second function includes a function of the difference and a phenomenological constant, and setting responsively to the positive determination includes setting the inspiration time equal to the second function of the difference and the phenomenological constant. For some applications, setting responsively to the positive determination includes determining the phenomenological constant at least in part responsively to at least one parameter of the first set of one or more parameters.

For some applications, setting responsively to the negative determination includes setting the inspiration time equal to a value within plus or minus 20% of the active expiration time, such as within plus or minus 10% of the active expiration time. For some applications, the third function includes a function of the active expiration time and a phenomenological constant, and setting responsively to the negative determination includes setting the inspiration time equal to the third function of the active inspiration time and the phenomenological constant. For some applications, setting responsively to the negative determination includes determining the phenomenological constant at least in part responsively to at least one parameter of the first set of one or more parameters.

For some applications, applying the algorithm to derive the inspiration time includes setting the inspiration time equal to a function of a difference between the breathing period and the active expiration time. For some applications, setting the inspiration time includes setting the inspiration time equal to a value within plus or minus 20% of the difference, such as within plus or minus 10% of the difference. For some applications, the function includes a function of the difference and a phenomenological constant, and setting the inspiration time includes setting the inspiration time equal to the function of the difference and the phenomenological constant. For some applications, setting the inspiration time includes determining the phenomenological constant at least in part responsively to at least one parameter of the first set of one or more parameters.

For some applications, applying the algorithm to derive the inspiration time includes setting the inspiration time equal to a function of the active expiration time. For some applications, setting the inspiration time includes setting the inspiration time equal to a value within plus or minus 20% of the active expiration time, such as plus or minus 10% of the active expiration time. For some applications, the function includes a function of the active expiration time and a phenomenological constant, and setting the inspiration time includes setting the inspiration time equal to the function of the active expiration time and the phenomenological constant. For some applications, setting the inspiration time includes determining the phenomenological constant at least in part responsively to at least one parameter of the first set of one or more parameters.

For some applications, the method includes analyzing the derived inspiration time to determine an amplitude of breathing during the inspiration time.

In an embodiment, deriving the expiratory airflow signal includes:

digitizing the raw signal to generate a digital signal;

performing spectral analysis on the digital signal to produce a frequency spectrum; and filtering the frequency spectrum to eliminate frequencies outside of a range of frequencies associated with expiratory airflow sounds.

For some applications, filtering the frequency spectrum includes setting the range to be between a first frequency and a second frequency, the first frequency between 30 and 50 Hz, and the second frequency between 100 and 200 Hz.

For some applications, filtering the frequency spectrum includes:

guiding the subject to perform breathing in a plurality of alternating inspiratory and expiratory respiration phases;

using the non-contact microphone, generating a raw calibration signal indicative of airflow sounds of the respiration during the respiration phases;

digitizing the raw calibration signal to generate a digital calibration signal, and performing spectral analysis on the digital calibration signal to produce an inspiration frequency spectrum and an expiration frequency spectrum;

subtracting the inspiration spectrum from the expiration spectrum to obtain a net frequency spectrum;

determining a first frequency and a second frequency by analyzing the net frequency spectrum; and setting the range to be between the first and second frequencies.

For some applications, determining the first and second frequencies includes:

setting the first frequency such that an area under a first portion of the net spectrum having a frequency less than the first frequency is less than a first percentage of a total area under the net spectrum; and setting the second frequency such that an area under a second portion of the net spectrum having a frequency greater than the second frequency is less than a second percentage of the total area under the net spectrum.

In an embodiment, deriving the expiratory airflow sound signal from the raw signal includes filtering the raw signal to eliminate frequencies outside of a range of frequencies associated with expiratory airflow sounds. For some applications, filtering the raw signal includes setting the range to be between a first frequency and a second frequency, the first frequency between 30 and 50 Hz, and the second frequency between 100 and 200 Hz.

In an embodiment, analyzing the raw signal includes setting a detection threshold, and deriving the expiratory airflow sound signal includes interpreting portions of the raw signal having a signal strength greater than the detection threshold as the expiratory airflow sound signal. For some applications, setting the detection threshold includes setting the detection threshold at a level sufficient to reduce erratic peaks in the raw signal that are not associated with functional breathing. For some applications, setting the detection threshold includes:

digitizing the raw signal to generate a digital signal having flow values at respective points in time, and buffering the flow values of the digital signal over a period of time;

transforming the buffered flow values into a histogram having a plurality of bins;

designating one of the bins having a greatest number of points as a maximum bin;

selecting two of the bins on opposite sides of the maximum bin;

setting a width of a noise band equal to a flow interval between the two bins; and setting the detection threshold responsively to a flow value of the maximum bin and the width of the noise band.

For some applications, setting the detection threshold includes setting the detection threshold equal to the flow value of the maximum bin plus a product of a constant and the width of the noise band.

In an embodiment, the method includes detecting sleep-disordered breathing by analyzing at least one parameter selected from: the first set of parameters, and the second set of estimated parameters. For some applications, the sleep-disordered breathing includes breathing associated with apnea, and detecting the sleep-disordered breathing includes detecting the apnea. For other applications, the sleep-disordered breathing includes breathing associated with sudden infant death syndrome (SIDS), and detecting the sleep-disordered breathing includes detecting the SIDS.

There is still further provided, in accordance with an embodiment of the present invention, a method for analyzing respiration of a subject, the method including:

generating a signal indicative of airflow sounds of the respiration;

guiding the subject to perform breathing in a plurality of respiration phases;

analyzing the signal during the guided respiration phases, and defining one or more parameters of a filter responsively to the analysis; and filtering background noise from the signal using the filter having the defined parameters.

In an embodiment, generating the signal includes generating the signal using a non-contact microphone.

for some applications, the one or more parameters of the filter include a signal-to-noise ratio, and defining the one or more parameters includes defining the signal-to-noise ratio.

In an embodiment, guiding the subject includes guiding the subject to perform breathing in a plurality of inspiratory and expiratory respiration phases. For some applications, guiding the subject includes guiding the subject to perform breathing in inspiratory, expiratory, and breath-holding respiration phases.

For some applications, defining the one or more parameters of the filter includes:

determining signal characteristics of background noise plus airflow sounds of inhalation, and of the background noise plus airflow sounds of exhalation;

determining net background noise responsively to the signal characteristics; and defining the one or more parameters of the filter responsively to the net background noise.

For some applications, the one or more parameters of the filter include a first frequency and a second frequency, analyzing the signal includes:

digitizing the signal to generate a digital signal, and performing spectral analysis on the digital signal to produce an inspiration frequency spectrum and an expiration frequency spectrum;

subtracting the inspiration spectrum from the expiration spectrum to obtain a net frequency spectrum; and determining the first and second frequencies by analyzing the net frequency spectrum, and filtering the background noise includes eliminating frequencies outside of a range of frequencies defined by the first and second frequencies.

For some applications, determining the first and second frequencies includes:

setting the first frequency such that an area under a first portion of the net spectrum having a frequency less than the first frequency is less than a first percentage of a total area under the net spectrum; and setting the second frequency such that an area under a second portion of the net spectrum having a frequency greater than the second frequency is less than a second percentage of the total area under the net spectrum.

There is yet further provided, in accordance with an embodiment of the present invention, a method for analyzing respiration of a subject, the method including:

determining an active expiration time and a breathing period of the subject;

determining whether a difference between the breathing period and the active expiration time is greater than or equal to a first function of the active expiration time;

responsively to a positive determination, estimating that an inspiration time of the subject is equal to a second function of the difference; and responsively to a negative determination, estimating that the inspiration time is equal to a third function of the active expiration time.

In an embodiment, determining the active expiration time and the breathing period includes:

generating a raw signal indicative of airflow sounds of the respiration;

analyzing the raw signal to derive an expiratory airflow sound signal from the raw signal; and analyzing the expiratory airflow sound signal to determine the active expiration time and the breathing period.

For some applications, determining includes determining whether the difference between the breathing period and the active expiration time is greater than or equal to the active expiration time.

For some applications, setting responsively to the positive determination includes setting the inspiration time equal to a value within plus or minus 20% of the difference, such as within plus or minus 10% of the difference. For some applications, the second function includes a function of the difference and a phenomenological constant, and setting responsively to the positive determination includes setting the inspiration time equal to the second function of the difference and the phenomenological constant. For some applications, setting responsively to the positive determination includes determining the phenomenological constant at least in part responsively to at least one parameter of the respiration.

For some applications, setting responsively to the negative determination includes setting the inspiration time equal to a value within plus or minus 20% of the active expiration time, such as within plus or minus 10% of the active expiration time. For some applications, the third function includes a function of the active expiration time and a phenomenological constant, and setting responsively to the negative determination includes setting the inspiration time equal to the third function of the active inspiration time and the phenomenological constant. For some applications, setting responsively to the negative determination includes determining the phenomenological constant at least in part responsively to at least one parameter of the respiration.

There is also provided, in accordance with an embodiment of the present invention, a method for analyzing respiration of a subject, the method including:

generating a raw signal indicative of airflow sounds of the respiration;

defining a detection threshold by:

digitizing the raw signal to generate a digital signal having flow values at respective points in time, and buffering the flow values of the digital signal over a period of time, transforming the buffered flow values into a histogram having a plurality of bins, designating one of the bins having a greatest number of points as a maximum bin, selecting two of the bins on opposite sides of the maximum bin, setting a width of a noise band equal to a flow interval between the two bins, and setting the detection threshold responsively to a flow value of the maximum bin and the width of the noise band; and deriving an expiratory airflow sound signal from the raw signal by interpreting portions of the raw signal having a signal strength greater than the detection threshold as the expiratory airflow sound signal.

For some applications, setting the detection threshold includes setting the detection threshold equal to the flow value of the maximum bin plus a product of a constant and the width of the noise band.

There is yet additionally provided, in accordance with an embodiment of the present invention, a method including:

using a non-contact microphone integrated into a ventilator, generating a signal indicative of airflow sounds of respiration of a subject; and analyzing the signal to detect active expiration of the subject.

For some applications, the method includes analyzing the active expiration to determine whether the ventilator is functioning properly.

For some applications, analyzing the signal includes analyzing a low-frequency component of the signal to detect the active respiration.

For some applications, generating the signal includes generating the signal during weaning of the subject from ventilation.

There is still additionally provided, in accordance with an embodiment of the present invention, a method including:

using a non-contact microphone integrated into a drug inhaler, generating a signal indicative of airflow sounds of respiration of a subject; and analyzing the signal to detect active expiration of the subject.

For some applications, the method includes guiding the subject to perform breathing in a plurality of respiration phases determined at least in part responsively to the detected active expiration.

For some applications, analyzing the signal includes analyzing a low-frequency component of the signal to detect the active respiration.

There is yet additionally provided, in accordance with an embodiment of the present invention, a method including:

selecting a subject suffering from insomnia;

using a non-contact microphone, generating a signal indicative of airflow sounds of respiration of the subject;

analyzing the signal to detect active expiration of the subject; and treating the insomnia by guiding the subject to perform breathing in a plurality of respiration phases determined at least in part responsively to the detected active expiration.

There is still additionally provided, in accordance with an embodiment of the present invention, apparatus for analyzing respiration of a subject, including:

a non-contact microphone, adapted to generate a raw signal representing airflow sounds of the respiration; and a control unit, adapted to:

analyze the raw signal to determine a first set of one or more parameters of the respiration, and apply an algorithm to the first set of parameters to derive a second set of one or more estimated parameters of the respiration that are not generally directly measurable in the raw signal.

There is yet additionally provided, in accordance with an embodiment of the present invention, apparatus for analyzing respiration of a subject, including:

a microphone, adapted to generate a signal representing airflow sounds of the respiration;

an output generator; and a control unit, adapted to:

drive the output generator to guide the subject to perform breathing in a plurality of respiration phases, analyze the signal during the guided respiration phases, and define one or more parameters of a filter responsively to the analysis, and filter background noise from the signal using the filter having the defined parameters.

There is also provided, in accordance with an embodiment of the present invention, apparatus for modifying naturally-occurring multi-phase biorhythmic activity of a subject, the apparatus including:

a sensor, adapted to detect a signal indicative of the multi-phase biorhythmic activity;

a control unit, adapted to:

analyze the signal to determine one or more parameters of a filter, filter background noise from the signal using the filter having the parameters, and at least in part responsively to the filtered signal, determine a stimulus input which is operative to change at least one aspect of the biorhythmic activity of the subject; and a stimulator, adapted to provide the stimulus input to the subject.

There is further provided, in accordance with an embodiment of the present invention, apparatus for analyzing respiration of a subject, the apparatus including a control unit, adapted to:

determine an active expiration time and a breathing period of the subject, determine whether a difference between the breathing period and the active expiration time is greater than or equal to a first function of the active expiration time, responsively to a positive determination, estimate that an inspiration time of the subject is equal to a second function of the difference, and responsively to a negative determination, estimate that the inspiration time is equal to a third function of the active expiration time.

There is still further provided, in accordance with an embodiment of the present invention, apparatus for analyzing respiration of a subject, the apparatus including:

a sensor, adapted to generate a raw signal indicative of airflow sounds of the respiration; and a control unit, adapted to:

define a detection threshold by:

digitizing the raw signal to generate a digital signal having flow values at respective points in time, and buffering the flow values of the digital signal over a period of time, transforming the buffered flow values into a histogram having a plurality of bins, designating one of the bins having a greatest number of points as a maximum bin, selecting two of the bins on opposite sides of the maximum bin, setting a width of a noise band equal to a flow interval between the two bins, and setting the detection threshold responsively to a flow value of the maximum bin and the width of the noise band, and derive an expiratory airflow sound signal from the raw signal by interpreting portions of the raw signal having a signal strength greater than the detection threshold as the expiratory airflow sound signal.

There is additionally provided, in accordance with an embodiment of the present invention, apparatus for use with a ventilator, the apparatus including:

a non-contact microphone, adapted to be integrated into the ventilator, and to generate a signal indicative of airflow sounds of respiration of a subject; and a control unit, adapted to analyze the signal to detect active expiration of the subject.

There is yet additionally provided, in accordance with an embodiment of the present invention, apparatus for use with a drug inhaler, the apparatus including:

a non-contact microphone, adapted to be integrated into the drug inhaler, and to generate a signal indicative of airflow sounds of respiration of a subject; and a control unit, adapted to analyze the signal to detect active expiration of the subject.

The present invention will be more fully understood from the following detailed description of embodiments thereof, taken together with the drawings, in which:

BRIEF DESCRIPTION OF THE DRAWINGS

FIG. 1 is a schematic pictorial illustration of a microphone-based breathing pattern modification system applied to a user, in accordance with an embodiment of the present invention;

FIG. 2 is a schematic block diagram of the system of FIG. 1, in accordance with an embodiment of the present invention;

FIG. 3 is a flow chart illustrating a method for determining a breathing pattern from a raw analog signal, in accordance with an embodiment of the present invention;

DETAILED DESCRIPTION OF EMBODIMENTS

Figures 4A, 4B:
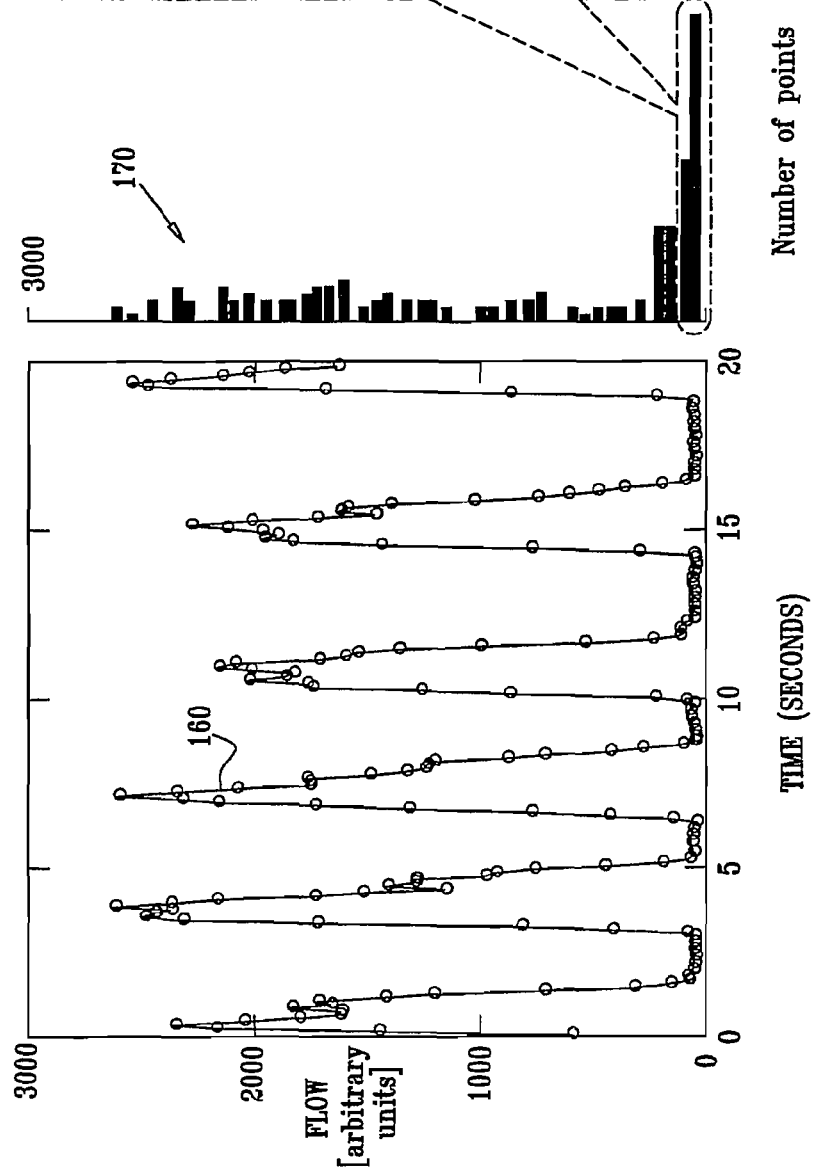
FIGS. 4A and 4B are schematic illustrations of signals analyzed at a threshold calculation step of the method of FIG. 3, in accordance with an embodiment of the present invention.

FIG. 1 is a schematic pictorial illustration of a microphone-based breathing pattern modification system 10 applied to a user 20, in accordance with an embodiment of the present invention. System 10 comprises a microphone 22 and a speaker 24, which typically are standard components of a standard headset or telephone. System 10 further comprises a control unit 26, which is coupled to microphone 22 and speaker 24 via a cable or wirelessly.

FIG. 2 is a schematic block diagram of system 10, in accordance with an embodiment of the present invention. Control unit 26 comprises an amplifier 28, an A/D converter 30, a CPU 32, and a sound synthesizer 34. Sound synthesizer 34 is typically adapted to generate tones, music, and/or synthesized or recorded oral messages.

For some applications, control unit 26 comprises a standard consumer electronics device, programmed in software to carry out the functions described herein. For example, control unit 26 may comprise a standard or pocket computer, a personal digital assistant (PDA), a "smart" phone, a telephone, or a cellular phone. Alternatively, at least a portion of the functions of control unit 26 are executed on a remote system that is accessed by a local device over a conventional wireless or wired network. Further alternatively, control unit 26 comprises a custom control unit produced to carry out the techniques described herein.

In general, a non-contact standard microphone in a headset designed for a human user can detect the sound of effortless breathing from two sources: (a) sound waves, typically at the frequency range of 500 to 5000 Hz, generated inside the body and propagated in the environment, such as speech, and (b) lower-frequency sound waves, which reflect turbulences generated by the airflow in the vicinity of the microphone during expiration and sometimes under windy conditions. Standard microphones are designed to detect speech, which is categorized in the first source (a). Speech is specific to the user's specific anatomy, typically can be detected anywhere in the vicinity of the user, and may be generated during inspiration and/or expiration. Sound of the second source (b) is usually considered to be noise that should be minimized (see, for example, U.S. Pat. No. 4,887,693 to Plice, which is incorporated herein by reference). Such sound is unrelated to the user's specific anatomy, is usually restricted to expiration only, and generally can be detected only if the microphone is placed in the path of the airflow.

FIG. 3 is a flow chart illustrating a method for determining a breathing pattern from a raw analog signal, in accordance with an embodiment of the present invention. Amplifier 28 amplifies a raw analog signal generated by microphone 22, at an amplification step 100, and A/D converter 30 digitizes the amplified signal, at a digitization step 102. Control unit 26 buffers the digital signal, at a buffer step 104. The size of the buffer is determined responsive to the requirements of the detection process. For example, if it is desired to perform spectral analysis as described hereinbelow every t seconds, and if data are sampled at a sampling rate f, then the buffer should typically be large enough to hold at least t*f data points.

At a filtering step 106, control unit 26 periodically performs spectral analysis on the buffered data, e.g., every 0.05-1 second (such as every 0.1 seconds). Control unit 26 typically performs the spectral analysis using a discrete Fourier transform (DFT), operating within a range of frequencies between a minimum frequency (fmin) and a maximum frequency (fmax). The minimum and maximum frequencies are typically determined based on characteristics of microphone 22 and the specific application. In general, the maximum frequency is set such that the spectral power at frequencies higher than the maximum frequency is dominated by sounds not associated with the airflow of expiration. The minimum frequency is generally set such that the spectral power at frequencies lower than the minimum frequency is dominated by environmental airflows, e.g., wind. Typically, at filtering step 106, control unit 26 eliminates frequencies that are less than a frequency f1 and greater than a frequency f2, where f1 is greater than minimum frequency fmin and f2 is less than maximum frequency fmax. For some applications, control unit 26 determines f1 and f2 using adaptive optimization techniques described hereinbelow with reference to FIGS. 8, 9A, and 9B. Alternatively, f1 and f2 are pre-selected (in which case the filtering is not adaptive). Typically, f1 is between about 30 and about 50 Hz, and f2 is between about 100 and about 200 Hz.

At a spectrum integration step 108, control unit 26 integrates the power of the spectrum, and, typically, smoothes the signal using a moving-average calculation, at a moving average calculation step 110. The resulting temporal (i.e., non-spectral) signal is indicative of the microphone-detected expiratory airflow. The control unit (a) buffers this signal at a buffer step 112, and (b) analyzes this signal at an expiratory airflow detection step 114, both of which are described hereinbelow.

At buffer step 112, control unit 26 buffers the temporal signals detected during the N most recent breathing periods. N is determined by the pattern parameters to assure that the data distribution is sufficient for threshold determination. For example, N may be selected to include at least five detected breathing periods, as shown hereinbelow in FIG. 4A.

At a threshold calculation step 116, using data stored at buffer step 112, control unit 26 calculates a detection threshold at selected time intervals, typically using the techniques described hereinbelow with reference to FIGS. 4A and 4B. For some applications, the detection threshold is set equal to the greater of (a) the threshold determined using the techniques described hereinbelow with reference to FIGS. 4A and 4B, and (b) a secondary threshold determined at step 118, as described hereinbelow. At expiratory airflow detection step 114, control unit 26 detects the onset and cessation of expiratory-related airflow by analyzing the microphone-detected airflow with respect to the detection threshold. The control unit interprets airflow having a signal strength greater than the detection threshold as expiration, and airflow having a signal strength less than the detection threshold as background noise.

For some applications, at expiratory airflow detection step 114, control unit 26 generates a real-time indication for user 20, indicating that expiration has been detected. For some applications, this indication helps user 20 optimize the positioning of microphone 22. Alternatively or additionally, if no respiration signal has been detected over a certain period of time, control unit 26 notifies user 20 that microphone 22 should be repositioned.

At a pattern determination step 118, control unit 26 determines breathing pattern parameters, such as described hereinbelow with reference to FIGS. 5, 6, and 7. In order to determine these parameters, it is desirable to have a sufficiently large number of recent breathing data points to process, and these are stored at buffer step 112. For example, if it is desired to have breathing data representative of five breaths, and if the most recent five breaths occurred over a 45 second period and were sampled at 10 Hz, then the buffer should typically contain at least 450 points. (Data processing techniques as are known in the art may be applied to reduce this number.)

In an embodiment, use of a secondary threshold at threshold calculation step 116, described hereinabove, reduces or eliminates erratic peaks that cannot be associated with functional breathing according to predetermined rules. For example, the secondary threshold may be used to identify erratic peaks in certain recorded signals that are associated with the user: (a) talking (rather than breathing), or (b) exhaling due to a change in posture, thereby forcing air out of his lungs (not as part of a functional breathing cycle).

As appropriate, control unit 26 may define and utilize one or more secondary thresholds by: (a) defining secondary thresholds responsive to one or more values associated with the previous 1-5 breaths (e.g., setting a secondary threshold to be n times larger than the average respiration volume associated with the breaths), (b) comparing the corresponding parameters for the currently-recorded breathing data with the secondary thresholds, and (c) accepting the currently-recorded breathing data as being indicative of actual functional breathing if the corresponding parameters do not pass the secondary thresholds. For some applications, control unit 26 determines a secondary threshold value at pattern determination step 118 (for example by taking a percentage, e.g., 20%, of the most recent average flow amplitude, as reflected in the breathing pattern and/or a series of breaths).

Reference is now made to FIGS. 4A and 4B, which are schematic illustrations of signals analyzed at threshold calculation step 116 (FIG. 3), in accordance with an embodiment of the present invention. FIG. 4A shows a trace 160 of the digitized microphone signal stored at buffer step 112 over a 20-second period. Trace 160 is transformed into a histogram 170, shown in FIG. 4B. Typically, this transformation is performed by setting the bin width of histogram 170 equal to the smallest value that results in at least one bin having at least a threshold number of points n, e.g., about 20 data points. Typically, the bin width is set such that a minimum or near-minimum number of the bins have at least the threshold number of points.

According to a first method for setting the bin width, control unit 26 sets an initial, transitional bin width to a low value, typically 1. The control unit counts the number of points in each resulting bin. If all the bins have fewer than n points, the control unit increments the transitional bin width, typically by 1, and the method loops back to the previous counting step. On the other hand, if any of the bins has at least n points, the control unit designates the bin having the greatest number of points M as a maximum bin 172.

According to a second method for setting the bin width, control unit 26 applies a successive-approximation procedure to the data of trace 160. The control unit creates an initial, transitional histogram, having a single bin having a flow data range between 0 and F, where F is the maximum flow value of trace 160. The control unit divides the flow data range into two equal flow intervals: (1) from 0 to F/2 and (2) from F/2 to F. The control unit selects the flow interval containing the larger number of points, and compares the number of points in the selected flow interval to n. If the number of points in the selected flow interval is greater than or equal to n, the method returns to the division step above, at which the selected flow interval is divided into two flow intervals. On the other hand, if the number of points in the selected flow interval is less than n, the control unit typically reverses the most recent division, resulting in a flow interval having M points, where M is greater than or equal to n. The control unit uses the resulting flow interval as the bin width of histogram 170. The control unit designates the bin of histogram 170 having the greatest number of points M as maximum bin 172.

Maximum bin 172 has a flow value (y-axis) of B. Flow value B typically corresponds to the average flow of the background noise of the signal. Typically, control unit 26 selects two bins 176 and 178 on opposite sides of maximum bin 172 having numbers of points closest to M/2, and sets a width W of a noise band 180 equal to the flow interval between bins 176 and 178. (Instead of using M/2, as described, for some applications a value of M/k is used, where k is typically between 1.5 and 4.) The control unit typically sets a detection threshold 182 equal to (a) B plus (b) the product of W and a constant, for example, equal to B plus an integer multiple of W, e.g., B+2W: Typically, control unit 26 determines detection threshold 182 substantially continuously, resulting in an adaptive detection process.

Figure 5:
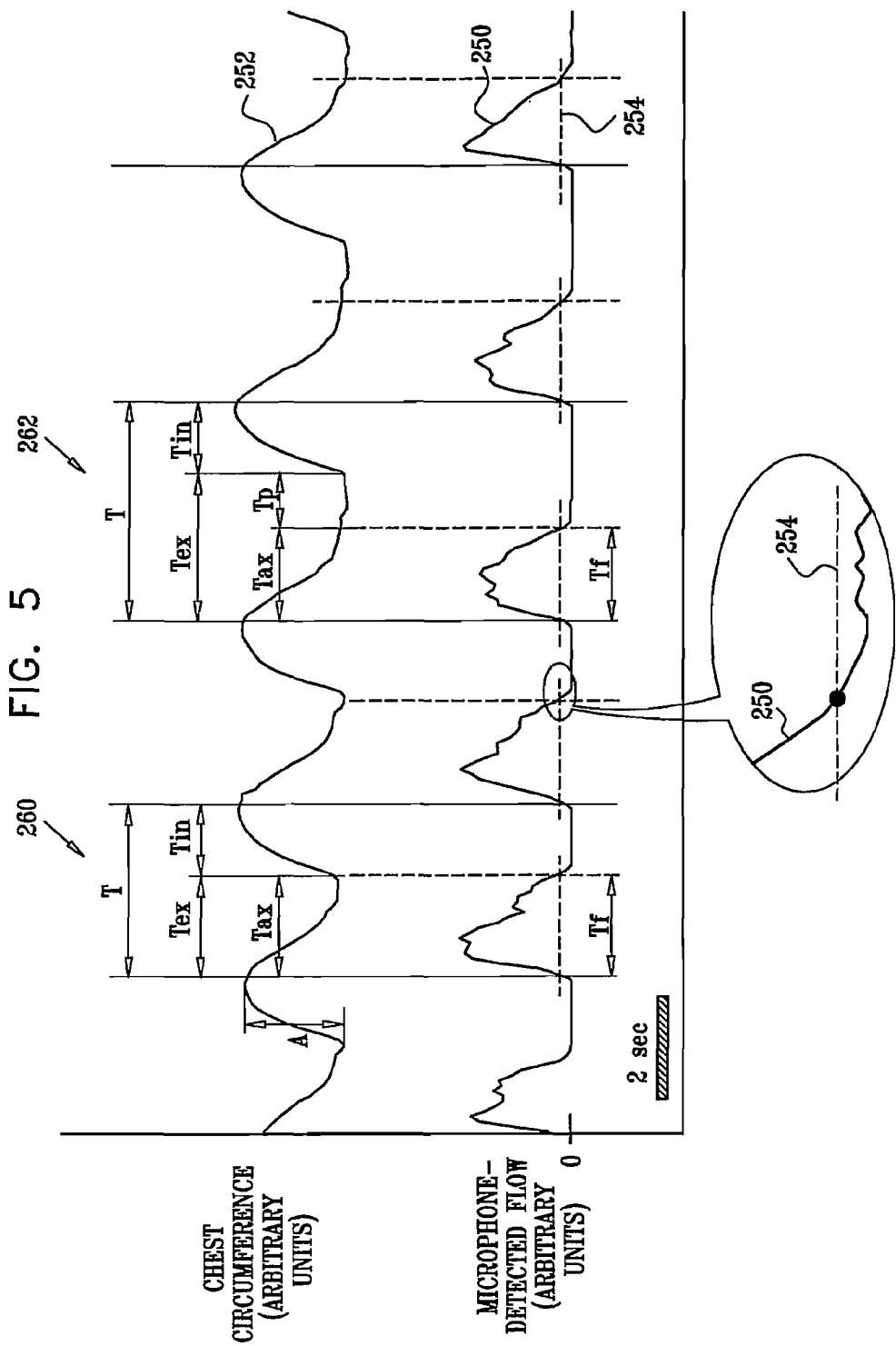
FIG. 5 is a schematic illustration of a recording of microphone-detected airflow, recorded using the techniques described herein, and a corresponding recording of chest circumference, recorded using techniques known in the art, in accordance with an embodiment of the present invention.

Reference is now made to FIG. 5, which is a schematic illustration of a recording 250 of microphone-detected airflow, recorded using the techniques described herein, and a corresponding recording 252 of chest circumference, recorded using techniques known in the art, in accordance with an embodiment of the present invention. Microphone-detected recording 250 and chest circumference recording 252 were recorded simultaneously in the same user. Microphone-detected recording 250 was filtered using frequencies f1 and f2 of 30 Hz and 150 Hz, respectively, at filtering step 106, described hereinabove with reference to FIG. 3. Chest circumference recording 252 was recorded using a belt-type sensor similar to the belt-type sensor described in the above-mentioned U.S. Pat. Nos. 5,423,328 and 6,090,037 to Gavish. Because such belt-type sensors produce highly accurate measurements of breathing phases, chest circumference recording 252 serves as a control for determining the accuracy of microphone-based breathing phase determinations using the techniques described herein.

Chest circumference recording 252 clearly shows all phases of normal breathing: inspiration and expiration, including active expiration and a post-expiratory pause. Chest circumference recording 252 is analyzed using min-max analysis to derive inspiration time $T_{in}$, breathing period T, expiration time $T_{ex}=T-T_{in}$, the active expiration time $T_{ax}$, and breathing amplitude A, for example as described in the above-mentioned U.S. Pat. No. 5,800,337.

In contrast, microphone-detected recording 250 shows only the active expiration phase of breathing. At least an estimation of inspiration time is necessary for certain applications (including breathing pattern modification by generating inspiration- and expiration-related guiding tones, as described, for example, in the above-referenced patents and patent application publications to Gavish and Gavish et al.).

Figure 6:
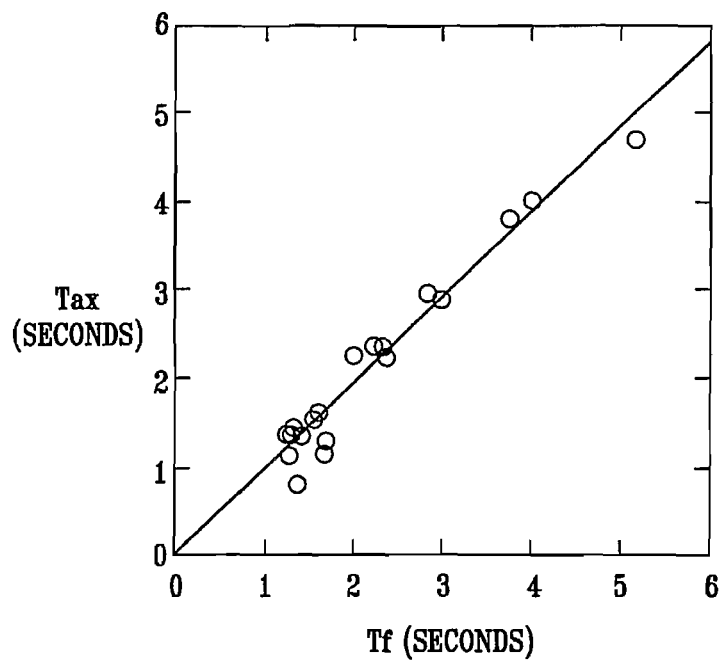
FIG. 6 shows an exemplary correlation between a microphone-detected expiration time and a belt-determined active expiration time, based on experimentally-obtained data like (but different from) the data shown in FIG. 5, in accordance with an embodiment of the present invention.

Reference is made to FIG. 6, which shows an exemplary correlation between microphone-detected expiration time $T_f$ and belt-determined active expiration time $T_{ax}$, using the data shown in FIG. 5, in accordance with an embodiment of the present invention. The correlation between $T_f$ and $T_{ax}$, as determined using linear regression, is r=0.98 with slope 0.97±0.05 (expected 1) and an intercept of nearly zero (expected 0). The accuracy in time is 0.22 seconds, where 0.14 seconds is the statistical error in measuring the time interval under a 10 Hz sampling rate. A similar correlation was found between the microphone-detected and belt-determined breathing periods (data not shown). These data indicate that the microphone-detected parameters are comparable to those detected by a belt-type sensor.

Reference is again made to FIG. 5. In an embodiment of the present invention, a method is provided for estimating inspiration time $T_{inf}$ using microphone-detected active expiration time $T_f$ and breathing period T (time between successive breaths). This method is typically used for carrying out pattern determination step 118, described hereinabove with reference to FIG. 3. The airflow signal reflected in recording 250 generally corresponds to the time derivative (with inverted sign) of the chest-circumference recording 252 during expiration, because airflow is the time derivative of lung volume as indicated by chest circumference.

The inventors have observed that effortless breathing generally can be characterized by one of two patterns:

a first pattern 260, in which the end of active expiration $T_{ax}$ occurs generally at the same time as the beginning of the subsequent inspiration $T_{in}$. For this pattern, $T_{inf}$ is estimated using the following formula:

$$T_{inf} = T - T_f \quad (1)$$

For some applications, $T_{inf}$ is set to a function of $T-T_f$. For example, $T_{inf}$ may be set to the product of $T-T_f$ and a constant between about 0.8 and about 1.2, such as between about 0.95 and about 1.05. Alternatively, $T_{inf}$ may be set to the sum of $T-T_f$ and the value, wherein the value is positive or negative. For some applications, $T_{inf}$ is set to be equal to $T-T_f$ within plus or minus 20%, such as within plus or minus 10%. For some applications, $T_{inf}$ is set to a phenomenological function of $T-T_f$, or of other respiration-related parameters measured using techniques described herein. For some applications, one or more constants of the phenomenological function is determined at least in part responsively to at least one parameter of the respiration.

a second pattern 262, in which the end of active expiration $T_{ax}$ is followed by a phase Tp with no chest movement, which is followed by the beginning of the subsequent inspiration $T_{in}$. For this pattern, $T_{inf}$ is typically estimated using the following formula:

$$T_{inf} = T_f \quad (2)$$

For some applications, $T_{inf}$ is set to a function of $T_f$. For example, $T_{inf}$ may be set to the product of $T_f$ and a constant between about 0.8 and about 1.2, such as between about 0.95 and about 1.05. Alternatively, $T_{inf}$ may be set to the sum of $T_f$ and the value, wherein the value is positive or negative. For some applications, $T_{inf}$ is set to be equal to $T_f$ within plus or minus 20%, such as within plus or minus 10%. For some applications, $T_{inf}$ is set to a phenomenological function of $T_f$, or of other respiration-related parameters measured using techniques described herein. For some applications, one or more constants of the phenomenological function is determined at least in part responsively to at least one parameter of the respiration.

The inventors have observed that in first pattern 260, active expiration time $T_{ax}$ generally has a duration greater than the duration of inspiration time $T_{in}$, sometimes up to 5 times greater. In contrast, in second pattern 262, $T_{ax}$ generally has a similar duration to that of $T_{in}$. The inventors have observed that first pattern 260 is usually obtained when a user is performing an action such as pursed lips breathing, i.e., artificially prolonging expiration by narrowing the gap between the lips, which is a known natural therapeutic maneuver. Second pattern 262 reflects a general natural tendency to match the flow at the beginning of inspiration and expiration.

Formulas (1) and (2) can be combined and represented by the following algorithm:

If $T-T_f \geq T_f$ then $T_{inf} = T-T_f$ else $T_{inf} = T_f$ \quad (3)

As mentioned above, for some applications, $T_{inf}$ is set to a function of $T-T_f$ or $T_f$, depending on the evaluation of the condition. Alternatively or additionally, the condition evaluated by the algorithm is: If $T-T_f \geq$ a function of $T_f$.

Figure 7:
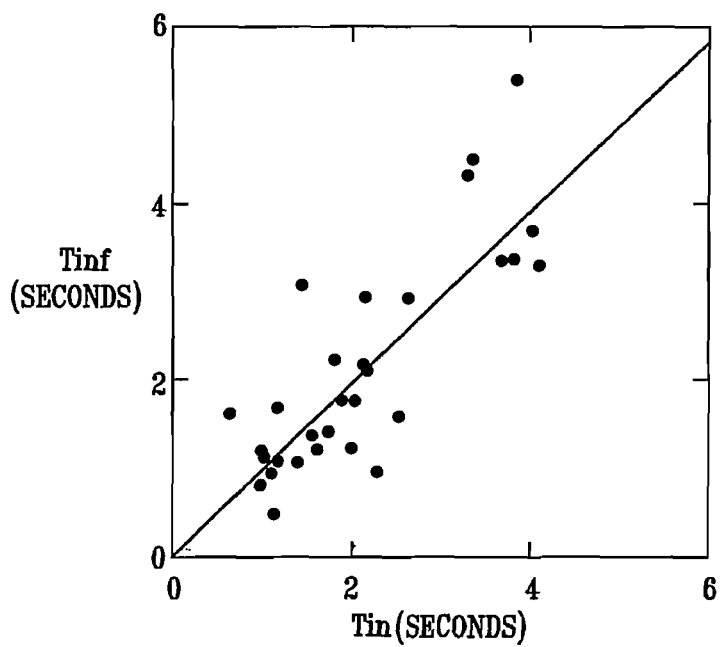
FIG. 7 is a graph showing experimental results measured in accordance with an embodiment of the present invention.

FIG. 7 is a graph showing experimental results measured in accordance with an embodiment of the present invention. The graph shows microphone-detected $T_{inf}$ calculated using algorithm (3) (y-axis) vs. $T_{in}$ measured with a belt-type sensor (x-axis), with the data points randomly selected from data of 10 different users (3 breaths for each user). The correlation between $T_{inf}$ and $T_{in}$, as determined using linear regression, is r=0.82 with slope 0.97±0.13 (expected 1) and an intercept of nearly zero (expected 0). The accuracy in time is 0.54 seconds, where 0.14 seconds is the statistical error in measuring the time interval under a 10 Hz sampling rate. This error represents about 25% of the average inspiration time $T_{in}$ of 2.1 seconds, and 7.8% of the average breathing period T of 6.9 seconds. These results are generally sufficiently accurate for the purpose of modifying breathing patterns by generating guiding tones. The nearly-unity slope between the parameters found using algorithm (3) and the belt-type sensor suggests that the differences are attributable to random data scattering. In an embodiment (typically during a breathing pattern modification procedure), the scattering is reduced to an acceptable level by averaging the value of T measured during multiple breathing cycles, and/or by averaging the value of $T_{inf}$ measured during multiple breathing cycles.

In an embodiment of the present invention, additional breathing parameters are derived from the microphone-detected airflow. The airflow can be expressed as Y(i,t), where Y is the magnitude of airflow, i is breath number, and t is the time extending from the beginning of breath i until the end of breath i. The additional breathing parameters include:

breathing amplitude, which is represented by the integrated airflow for a single breath, which is given by:

$$Af(i) = \sum_t Y(i, t) \quad (4)$$

The integrated airflow represents the depth of breathing for the $i^{th}$ breath. (Alternatively, breathing amplitude is represented by the maximum value of Y(i,t) over a suitable interval.)

the geometrical properties of the airflow pattern by means of moments, which is given by:

$$\sum_t (Y(i, t) \cdot (t - \langle ti \rangle)^n) \quad (5)$$

where:

-continued $$(a)\langle ti\rangle = \frac{\sum_t (Y(i,t)\cdot t)}{\sum_t Y(i,t)}, \text{ and}$$

(b) n is the order of the moment.

For example, if n=0, 1, 2, or 3, the sum corresponds, respectively, to (a) integrated area, (b) zero by definition, (c) variance of the airflow pattern, and (d) asymmetry of the airflow pattern.

For some applications, breathing amplitude is determined, such as described above, and at least one additional parameter is derived from the breathing amplitude. For example, the additional parameter may be: (a) a measure of ventilation (amount of air per unit time), such as a product of the breathing amplitude and the respiration period, or (b) a measure of breathing irregularity, such as relative fluctuations in breathing amplitude (e.g., the standard deviation of the n last breathing amplitude values, divided by the mean of the breathing amplitude). Breathing irregularity generally increases during stress and some diseases. For some applications, other characteristics of the airflow are detected, such as by fitting mathematical models having a physiological rationale, such as:

- a square pulse that corresponds to uniform expiration, which characterizes pursed lips breathing;
- a fast-rising but gradually decreasing flow followed by a post-expiratory pause, which characterizes relaxed breathing; or
- an exponential-decay that characterizes passive elastic recoil of the lungs against airways resistance.

For some applications, the airflow is analyzed to detect a characteristic of breathing with effort. For some applications, the airflow is analyzed to detect a characteristic of breathing during which the lungs undergo a functional change, such as when the subject suffers from asthma, emphysema, or another condition in which small airways collapse during expiration (which cannot be characterized as a simple elastic recoil).

Figure 8:
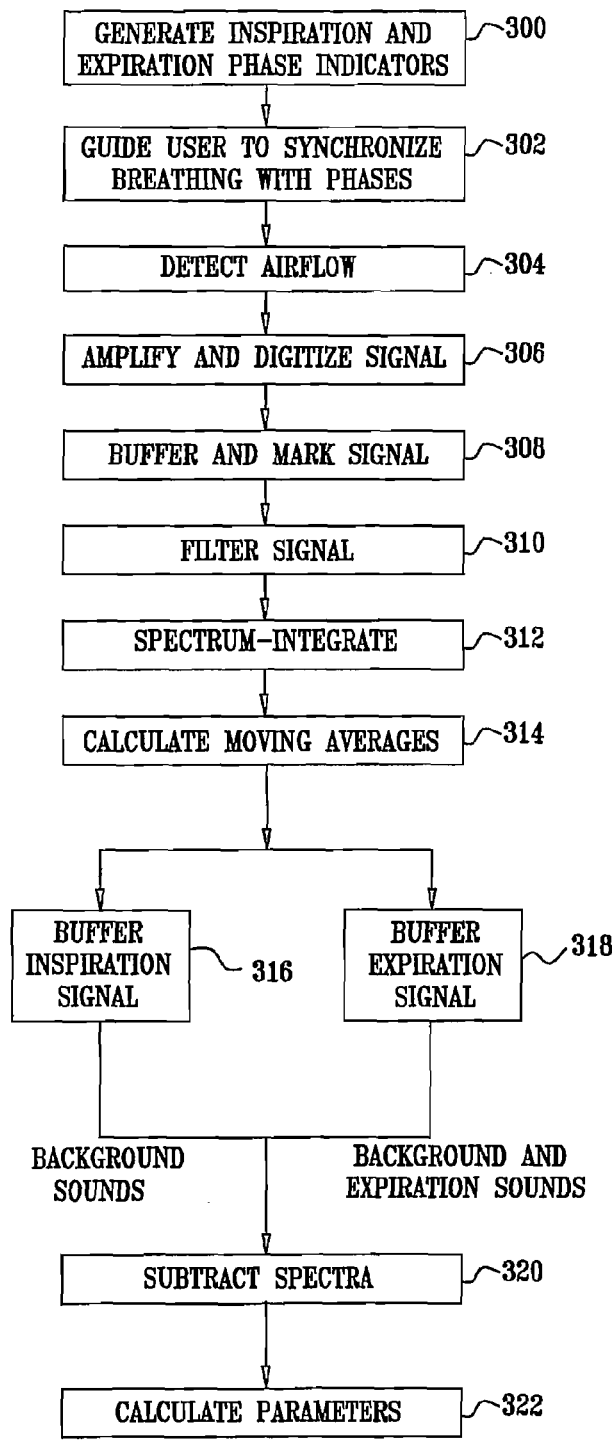
FIG. 8 is a flow chart illustrating a method for adaptively determining filtering frequencies, in accordance with an embodiment of the present invention.

FIG. 8 is a flow chart illustrating a method for adaptively determining filtering frequencies, in accordance with an embodiment of the present invention. For some applications, control unit 26 uses this method to determine filtering frequencies f1 and f2, described hereinabove with reference to filtering step 106 of FIG. 3, when system 10 is used for breathing pattern modification. Typically, when system 10 is turned on, or when airflow is undetected for a predetermined amount of time, control unit 26 automatically enters a metronome mode of operation. In this mode of operation, CPU 32 alternatingly generates inspiration and expiration phase indicators, at a phase indicators generation step 300. For example, CPU 32 may generate each inspiration phase indicator for between about 1 and about 5 seconds, e.g., about 2 seconds, and each expiration phase indicator for between about 2 and about 10 seconds, e.g., about 4 seconds. CPU 32 typically generates each of the phases between about 5 and about 10 times.

Responsively to the phase indicators, sound synthesizer 34 generates tones and/or oral messages that instruct user 20 to synchronize breathing with the inspiration and expiration phases, at a guide user step 302. Microphone 22 detects the resulting user-generated airflow, at an airflow detection step 304. Amplifier 28 amplifies the signal, and A/D converter 30 digitizes the amplified signal, at an amplification and digitization step 306. At a buffer and mark step 308, control unit 26 buffers the digital signal, and marks the buffered signal with the phase indicator generated when the signal was recorded.

At a filtering step 310, control unit 26 periodically performs spectral analysis on the buffered data, e.g., every 0.1 seconds. Control unit 26 typically performs the spectral analysis using a DFT, operating within a range of frequencies between fmin and fmax, as described hereinabove with reference to filtering step 106 of FIG. 3. Control unit 26 eliminates frequencies that are less than fmin and greater than fmax. At a spectrum integration step 312, control unit 26 integrates the power of separate spectrums for the signals stored during the inspiration phase and the expiration phase, respectively, and typically smoothes the signals using a moving-average calculation, at a moving average calculation step 314. The resulting inspiration and expiration spectra are separately buffered at an inspiration buffer step 316 and an expiration buffer step 318, respectively.

Figure 9A:
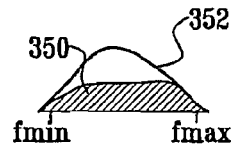
FIGS. 9A and 9B are schematic illustrations of several exemplary spectra, in accordance with an embodiment of the present invention.
Figure 9B:
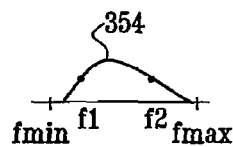

Reference is made to FIGS. 9A and 9B, which are schematic illustrations of several exemplary spectra, in accordance with an embodiment of the present invention. FIG. 9A shows an exemplary inspiration spectrum 350, and an exemplary expiration spectrum 352. At a spectra subtraction step 320 (FIG. 8), control unit 26 subtracts inspiration spectrum 350 from expiration spectrum 352 to obtain a net spectrum 354, shown in FIG. 9B, which is associated with expiratory airflow sounds. Control unit 26 typically averages net spectrum 352 over a selected number of guided breaths. At a parameter calculation step 322, control unit 26 calculates parameters of net spectrum 352, including f1 and f2, described hereinabove with reference to filtering step 106 of FIG. 3. The resulting parameters are used at filtering step 106, as described hereinabove with reference to FIG. 3. For some applications, f1 is set to a value such that the area under net spectrum 354 to the left of f1 is r1% (e.g., 10%) of the total area under net spectrum 354, and f2 is set to a value such that the area under net spectrum 354 to the right of f2 is r2% (e.g., 10%) of the total area under net spectrum 354. As appropriate, r1 may be equal or not equal to r2. Alternatively or additionally, control unit 26 derives other parameters of net spectrum 354 that are used for filtering at filtering step 106 of FIG. 3.

Reference is again made to FIG. 1. In an embodiment of the present invention, microphone 22 is integrated into a medical device in fluid communication (e.g., via air or another gas) with respiration-related airflow of user 20. For example, the medical device may comprise a breathing mask or a tube, such as a tracheotomy tube. For some applications, the breathing mask or tube are components of a ventilator that applies positive pressure to the lungs of user 20. The techniques described herein are used to detect proper performance of the ventilator, typically by detecting active expiration by the user. Active expiration is typically measured by detecting low-frequency sounds indicative of expiratory airflow, rather than by detecting sounds of breathing. (In such subject, sounds of breathing often do not correlate with expiration, because the sounds of breathing are often affected by various constrictions in the subject's airways. However, low-frequency sounds indicative of expiratory airflow are not generally affected by such constrictions.) For some applications, the techniques described herein are used for non-contact monitoring of breathing during weaning from ventilation.

In an embodiment of the present invention, the techniques described herein are used for non-contact monitoring of breathing during use of a drug inhaler by the subject. Typically, microphone 22, and, optionally, other components of system 10, are integrated into the drug inhaler. For some applications, such non-contact monitoring of breathing is combined with techniques for modifying breathing activity of the subject, such as those described in the above-mentioned patent and patent application publications to Gavish and Gavish et al.

In an embodiment of the present invention, the techniques described herein and/or in the above-mentioned patent and patent application publications to Gavish and Gavish et al. are used to treat a subject suffering from insomnia. Insomnia is sometimes caused by disordered breathing, such as fast and shallow breathing. For some applications, insomnia is treated using techniques described herein for detecting and monitoring breathing, in combination with techniques for modifying respiration-related biorhythmic activity of the subject described in the above-mentioned patent and patent application publications to Gavish and Gavish et al.

In an embodiment of the present invention, the breathing monitoring techniques described herein are used for detecting sleep-disordered breathing, such as sleep-disordered breathing associated with sleep apnea or sudden infant death syndrome (SIDS). Typically, breath-by-breath airflow during exhalation is monitored. For some applications, such non-contact monitoring of breathing is combined with techniques for modifying breathing activity of the subject, such as those described in the above-mentioned patent and patent application publications to Gavish and Gavish et al.

In an embodiment of the present invention, techniques described herein are used in combination with techniques for modifying biorhythmic activity of user 20. Typically, the biorhythmic activity includes respiration. The user is guided to inhale for a certain period of time, exhale for a certain period of time, and, optionally, to hold his breath for a certain period of time.

In an embodiment of the present invention, a method is provided for modifying naturally-occurring multi-phase biorhythmic activity of a subject, such as respiration of the subject. The method comprises detecting a signal indicative of the multi-phase biorhythmic activity, and analyzing the signal to determine one or more parameters of a filter. Background noise is filtered from the signal using the filter. At least in part responsively to the filtered signal, a stimulus input, such as an audio and/or visual stimulus input, is determined which is operative to change at least one aspect of the biorhythmic activity of the subject, and the stimulus input is provided to the subject. For some applications, the background noise is indicative of secondary biorhythmic activity different from the multi-phase biorhythmic activity, and the secondary biorhythmic activity-related background noise is filtered from the signal.

For some applications, the background noise is filtered from the signal by frequency filtering the signal. Alternatively or additionally, the signal is filtered by performing spectral analysis on the signal to produce a frequency spectrum. For example, the frequency spectrum may be frequency filtered. Further alternatively, non-frequency spectral analysis is performed on the signal in order to classify the signal according to one or more variables.

For some applications, the background noise is filtered to remove non-frequency-related noise from the signal, typically to eliminate a portion of the signal that is not relevant to determining to the stimulus input. For example, a breathing-related signal (e.g., monitored using a belt-type sensor) may include a heartbeat-related component which is noise with respect to the respiration-related component of the signal. This heartbeat-related component is eliminated from the signal, typically using non-frequency-related filtering, such as by identifying small peaks characteristic of the heartbeats and removing them from the signal.

As appropriate, techniques described herein are practiced in conjunction with techniques described in the above-mentioned patents and patent application publications to Gavish and Gavish et al.

Although metronome stimuli and/or other instructions have generally been described herein as including audio tones and/or oral messages, such stimuli and instructions may also take additional forms, such as visual display images, e.g., text messages (e.g., "inhale" and "exhale"), and/or dynamically changing graphical features, e.g., color and form. In such cases, sound synthesizer 34 and speaker 24 are replaced with an appropriate output generator. Alternatively, sound synthesizer 34 generates oral guiding messages only, rather than tones.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for modifying naturally-occurring multi-phase biorhythmic activity of a subject, the method comprising:
   detecting, using a sensor, a signal indicative of the multi-phase biorhythmic activity;
   analyzing, using a control unit, the signal to determine one or more parameters of a filter;
   filtering, using the control unit, background noise from the signal using the filter having the parameters;
   at least in part responsively to the filtered signal, determining, using the control unit, a stimulus input which is operative to change at least one aspect of the biorhythmic activity of the subject; and
   providing the stimulus input to the subject, using a stimulator,
   wherein the multi-phase biorhythmic activity includes respiration of the subject, and wherein detecting the signal comprises detecting the signal indicative of the respiration.

2. The method according to claim 1, wherein filtering the background noise comprises frequency filtering the signal.

3. The method according to claim 1, wherein filtering the background noise comprises performing non-frequency spectral analysis on the signal in order to classify the signal according to one or more variables.

4. The method according to claim 1, wherein the background noise is indicative of secondary biorhythmic activity different from the multi-phase biorhythmic activity, and wherein filtering the background noise from the signal comprises filtering the secondary biorhythmic activity-related background noise from the signal.

5. The method according to claim 1, wherein the background noise includes a heartbeat-related component of the signal, and wherein filtering the background noise from the signal comprises filtering the heartbeat-related component from the signal.

6. The method according to claim 1, wherein filtering the background noise comprises removing non-frequency-related noise from the signal.

7. A method for modifying naturally-occurring multi-phase biorhythmic activity of a subject, the method comprising:
   detecting, using a sensor, a signal indicative of the multi-phase biorhythmic activity;

analyzing, using a control unit, the signal to determine one or more parameters of a filter;

filtering, using the control unit, background noise from the signal using the filter having the parameters;

at least in part responsively to the filtered signal, determining, using the control unit, a stimulus input which is operative to change at least one aspect of the biorhythmic activity of the subject; and providing the stimulus input to the subject, using a stimulator, wherein filtering the background noise comprises performing spectral analysis on the signal to produce a frequency spectrum.

8. The method according to claim 7, wherein performing the spectral analysis comprises frequency filtering the frequency spectrum.

9. The method according to claim 6, wherein the non-frequency-related noise includes a heartbeat-related component of the signal, and wherein removing the non-frequency-related noise comprises removing the heartbeat-related component of the signal from the signal.

10. Apparatus for modifying naturally-occurring multi-phase biorhythmic activity of a subject, the apparatus comprising:

a sensor, adapted to detect a signal indicative of the multi-phase biorhythmic activity;

a control unit, adapted to:
  analyze the signal to determine one or more parameters of a filter,
  filter background noise from the signal using the filter having the parameters, and
  at least in part responsively to the filtered signal, determine a stimulus input which is operative to change at least one aspect of the biorhythmic activity of the subject; and a stimulator, adapted to provide the stimulus input to the subject, wherein the multi-phase biorhythmic activity includes respiration of the subject, and wherein the sensor is adapted to detect the signal indicative of the respiration.

11. The apparatus according to claim 10, wherein the control unit is adapted to filter the background noise by frequency filtering the signal.

12. The apparatus according to claim 10, wherein the control unit is adapted to filter the background noise by performing non-frequency spectral analysis on the signal in order to classify the signal according to one or more variables.

13. The apparatus according to claim 10, wherein the background noise is indicative of secondary biorhythmic activity different from the multi-phase biorhythmic activity, and wherein the control unit is adapted to filter the secondary biorhythmic activity-related background noise from the signal.

14. The apparatus according to claim 10, wherein the background noise includes a heartbeat-related component of the signal, and wherein the control unit is adapted to filter the heartbeat-related component from the signal.

15. The apparatus according to claim 10, wherein the control unit is adapted to filter the background noise by removing non-frequency-related noise from the signal.

16. Apparatus for modifying naturally-occurring multi-phase biorhythmic activity of a subject, the apparatus comprising:

a sensor, adapted to detect a signal indicative of the multi-phase biorhythmic activity;

a control unit, adapted to:
  analyze the signal to determine one or more parameters of a filter,
  filter background noise from the signal using the filter having the parameters, and
  at least in part responsively to the filtered signal, determine a stimulus input which is operative to change at least one aspect of the biorhythmic activity of the subject; and a stimulator, adapted to provide the stimulus input to the subject, wherein the control unit is adapted to filter the background noise by performing spectral analysis on the signal to produce a frequency spectrum.

17. The apparatus according to claim 16, wherein the control unit is adapted to frequency filter the frequency spectrum.

18. The apparatus according to claim 15, wherein the non-frequency-related noise includes a heartbeat-related component of the signal, and wherein the control unit is adapted to remove the heartbeat-related component of the signal from the signal.

* * * * *